(12) United States Patent
Carrasquillo et al.

(10) Patent No.: US 10,459,249 B2
(45) Date of Patent: *Oct. 29, 2019

(54) CHIRAL SCLERAL LENSES

(71) Applicant: Boston Foundation for Sight, Needham, MA (US)

(72) Inventors: Karen G. Carrasquillo, Arlington, MA (US); Chirag Patel, Boston, MA (US); Crystal Remington, Northborough, MA (US); Alan Kwok, Arlington, MA (US); Deborah S. Jacobs, Brookline, MA (US)

(73) Assignee: Boston Foundation for Sight, Needham, MA (US)

( * ) Notice: Subject to any disclaimer, the term of this patent is extended or adjusted under 35 U.S.C. 154(b) by 9 days.

This patent is subject to a terminal disclaimer.

(21) Appl. No.: 15/833,001

(22) Filed: Dec. 6, 2017

(65) Prior Publication Data

US 2018/0157064 A1 Jun. 7, 2018

Related U.S. Application Data

(63) Continuation of application No. 15/235,838, filed on Aug. 12, 2016, now Pat. No. 9,874,766.

(60) Provisional application No. 62/250,480, filed on Nov. 3, 2015.

(51) Int. Cl.
*G02C 7/04* (2006.01)
*A61B 3/04* (2006.01)

(52) U.S. Cl.
CPC ............. *G02C 7/047* (2013.01); *A61B 3/04* (2013.01); *G02C 2202/08* (2013.01)

(58) Field of Classification Search
CPC ................. G02C 7/047; G02C 7/049

USPC .................................................... 351/159.23
See application file for complete search history.

(56) References Cited

U.S. PATENT DOCUMENTS

| 2,641,161 A | 6/1953 | Silverstein |
| 3,495,899 A | 2/1970 | Biri |
| 5,062,701 A | 11/1991 | Drazba et al. |
| 5,114,628 A | 5/1992 | Hofer et al. |
| 5,570,142 A | 10/1996 | Lieberman |

(Continued)

FOREIGN PATENT DOCUMENTS

| EP | 0151762 A2 | 8/1985 |
| EP | 1372019 A1 | 12/2003 |
| GB | 2132785 A | 7/1984 |

OTHER PUBLICATIONS

Caroline et al., "Scleral Lenses Do Not Center", Contact Lens Spectrum, Aug. 1, 2014, 3 pages.

(Continued)

*Primary Examiner* — Darryl J Collins
(74) *Attorney, Agent, or Firm* — Wilmer Cutler Pickering Hale and Dorr LLP

(57) ABSTRACT

The present disclosure relates to trial scleral lenses, and the resulting scleral lenses, designed for the asymmetric shape of the sclera and/or its chiral properties. In some embodiments, the scleral lenses are also designed for the specific asymmetry associated with different scleral diameters. In addition, as discussed herein, the scleral shape can vary with different conditions of the eye. By designing a set of trial scleral lenses that takes into account these different asymmetric properties of the sclera, a clinician can be more efficient, fitting more eyes with fewer subsequent modifications. The resulting lenses will also achieve a better fit.

52 Claims, 11 Drawing Sheets

(56) References Cited

U.S. PATENT DOCUMENTS

| | | | |
|---|---|---|---|
| 5,835,187 | A | 11/1998 | Martin |
| 7,270,412 | B2 | 9/2007 | Legerton et al. |
| 7,338,160 | B2 | 3/2008 | Lieberman et al. |
| 7,717,555 | B2 | 5/2010 | Legerton et al. |
| 7,862,176 | B2 | 1/2011 | Gemoules et al. |
| 8,042,943 | B2 | 10/2011 | Legerton et al. |
| 8,057,035 | B2 | 11/2011 | Legerton et al. |
| 8,083,346 | B2 | 12/2011 | Legerton |
| 8,113,653 | B2 | 2/2012 | Legerton et al. |
| 8,118,426 | B2 | 2/2012 | Cotie et al. |
| 8,366,272 | B1 | 2/2013 | Myhill et al. |
| 8,500,273 | B2 | 8/2013 | Tung |
| 8,632,188 | B1 | 1/2014 | Gemoules |
| 9,016,863 | B2 | 4/2015 | Gemoules |
| 2010/0123875 | A1 | 5/2010 | Gemoules et al. |
| 2010/0128224 | A1 | 5/2010 | Legerton |
| 2010/0245759 | A1 | 9/2010 | Legerton et al. |
| 2010/0271589 | A1 | 10/2010 | Legerton et al. |
| 2013/0297015 | A1 | 11/2013 | Johns et al. |
| 2014/0074230 | A1 | 3/2014 | Blum |
| 2015/0088297 | A1 | 3/2015 | Gemoules |
| 2015/0131055 | A1 | 5/2015 | Catanzariti et al. |

OTHER PUBLICATIONS

Gemoules, "A Novel Method of Fitting Scleral Lenses Using High Resolution Optical Coherence Tomography", Eye & Contact Lens, vol. 34, No. 2, pp. 80-83, (2008).

Hall, "What You Need to Know About Sagittal Height and Scleral Lenses", Contact Lens Spectrum, May 1, 2015, 8 pages.

Healio Primary Care Optometry News: Meeting News Coverage, "Diagnostic fitting still best method for scleral lenses, researchers say", May 15, 2014, 2 pages.

International Search Report and Written Opinion dated Nov. 17, 2016, in the International application No. PCT/US16/46804, filed Aug. 12, 2016, 9 pages.

Kojima et al., "Eye Shape and Scleral Lenses", Contact Lens Spectrum, Apr. 1, 2013, 9 pages.

Le et al., "Pilot Study for OCT Guided Design and Fit of a Prosthetic Device for Treatment of Corneal Disease", Hindawi Publishing Corporation, Journal of Ophthalmology, vol. 2012, Article ID 812034, (2012), 7 pages.

Ritzmann et al., "Understanding Scleral Shape with the Eaglet Eye Surface Profiler", Pacific University College of Optometry, Forest Grove, Oregon and FALCO Contact Lens, Tagerwilen Switzerland, poster retrieved from [http://www.pentavisionevents.com/ckfinder/userfiles/files/Ritzman%20-%20Understanding%20Scleral%20Shape%20with%20the%20Eaglet%20Eye%20Surface%20Profiler.pdf], 3 pages.

Schornack, "Scleral Lenses: A Literature Review", Eye & Contact Lens, vol. 41, No. 1, Jan. 2015, pp. 3-11.

Smolek et al., "Inattention to Nonsuperimposable Midline Symmetry Causes Wavefront Analysis Error", Arch Ophthalmol, vol. 120, pp. 439-447, Apr. 2002.

Van der Worp E., "A Guide to Scleral Lens Fitting", Version 2.0 [monograph online]. Forest Grove, OR: Pacific University; (2015), Available from: [http://commons.pacificu.edu/mono/10/], 77 pages.

Visionary Optics, Jupiter Scleral: the ultimate tool for irregular corneas, First published online in Oct. 2011, 4 pages.

RIGHT EYE

|  | 18mm | 18.5mm | 19.0mm |
|---|---|---|---|
| 3 SAG HEIGHT VALUES (mm) | STD 2.6, 3.0, 3.4 | STD 2.6, 3.0, 3.4 | STD 2.6, 3.0, 3.4 |
| 3 SAG HEIGHT VALUES (mm) | FLAT 2.6, 3.0, 3.4 | FLAT 2.6, 3.0, 3.4 | FLAT 2.6, 3.0, 3.4 |
| 3 SAG HEIGHT VALUES (mm) | STEEP 2.6, 3.0, 3.4 | STEEP 2.6, 3.0, 3.4 | STEEP 2.6, 3.0, 3.4 |

LEFT EYE

|  | 18mm | 18.5mm | 19.0mm |
|---|---|---|---|
| 3 SAG HEIGHT VALUES (mm) | STD 2.6, 3.0, 3.4 | STD 2.6, 3.0, 3.4 | STD 2.6, 3.0, 3.4 |
| 3 SAG HEIGHT VALUES (mm) | FLAT 2.6, 3.0, 3.4 | FLAT 2.6, 3.0, 3.4 | FLAT 2.6, 3.0, 3.4 |
| 3 SAG HEIGHT VALUES (mm) | STEEP 2.6, 3.0, 3.4 | STEEP 2.6, 3.0, 3.4 | STEEP 2.6, 3.0, 3.4 |

FIG. 6

CHIRAL SCLERAL LENSES

CROSS REFERENCE TO RELATED APPLICATIONS

This application is a continuation of U.S. application Ser. No. 15/235,838, filed Aug. 12, 2016, which claims priority under 35 U.S.C. § 119(e) to U.S. Provisional Application No. 62/250,480, filed Nov. 3, 2015, entitled "Chiral Trial Scleral Lenses," the content of which are incorporated herein in their entirety.

FIELD OF THE DISCLOSURE

The present disclosure relates generally to trial scleral lenses that are designed to achieve fit in more eyes with fewer subsequent modifications and the resulting scleral lenses that are designed to achieve better fit.

BACKGROUND

Many people suffer from eye conditions and diseases that can be corrected or treated with lenses that vault the cornea and rest on the sclera (referred to herein as "scleral lenses"). These lenses are distinguished from the more common corneal contact lenses which rest on the cornea. For reference, an illustration depicting a scleral lens vaulting over an irregular cornea and resting on the sclera is shown in FIG. 1. As shown in FIG. 1, sclera 105 refers to the dense, white, fibrous outer layer of the eyeball that is continuous with the cornea 112 at the front of the eye. A scleral lens 120 rests on the sclera 105 and vaults the cornea 112 with a reservoir 115 that is filled with artificial tears at the time of application. Modern scleral lenses are made of gas-permeable plastic that allows for transmission of atmospheric oxygen, and are characterized by a shape that allows for retention of fluid in the reservoir and tear exchange, 115 so as to meet the underlying cornea's physiologic needs.

FIG. 2 shows certain scleral lens parameters that characterize the design of a scleral lens. The sagittal height 210 refers to the perpendicular distance between the diameter at the 12 mm chord 245 and the apex 225. The haptic angle 220 refers to an angle between a straight (reference) tangent line 230 and a diameter of the scleral lens. This angle can characterize the relationship between the haptic portion and transitional zone 235 of the scleral lens. The haptic zone 240 refers to the portion of the lens that rests on the sclera.

Corneal contact lenses can be fitted using an "empiric" approach, in which measurements of the contour of the cornea are obtained, and on that basis a lens is selected or designed for the eye. The instruments used to measure the eye do not have the range to take measurements for the larger scleral diameter. Furthermore, these instruments depend on transparency or reflection, neither of which is characteristic of the scleral portion of the eye. Typically, scleral lenses are fitted to the individual eye in a "diagnostic" approach, in which a trial lens is placed on the eye and fit is assessed. This process is iterative with subsequent trial lenses selected, modified, or designed to address deficiencies of the prior trial lens. Typically, multiples trial lenses and wearing trials are required. Ill-fitting lenses may not meet the visual needs of the patient and can compromise the health of the eye. Some eyes cannot be fitted because of the unique contour and/or constraints intrinsic to the design and manufacture of scleral lenses. However, this may not be apparent until many scleral lens fitting and wearing trials are undertaken for that eye.

SUMMARY

The present disclosure relates generally to trial scleral lenses designed to achieve fit in more eyes with fewer modifications per eye and the resulting scleral lenses that are designed to achieve better fit. In some embodiments of the present disclosure, the trial scleral lenses allow for satisfactory fit based on a trial of 1-3 trial lenses per eye. One embodiment can include a design that takes into account the specific asymmetry and chiral properties common to the shape and or anatomy of the eye, as well as the specific asymmetry and chiral properties associated with different scleral diameters and ocular conditions and diseases. The design for the trial scleral lenses can also include at least three different haptic or hemi-meridian configurations: standard, steep and flat. The embodiments described herein can include additional features. For example, the trial scleral lenses can be designed in a range of sagittal heights and a range of scleral diameters. In some examples, the trial scleral lenses do not require a chiral pair. Further, the design of the trial scleral lenses may incorporate aspheric front surface optics to meet the optical demands of an individual eye.

In one embodiment, a set of trial scleral lenses can include a right lens configured with four specified hemi-meridian contours that each corresponds to a rotationally asymmetric hemi-meridian characteristic of a right eye and a left lens configured with four specified hemi-meridian contours that each corresponds to a rotationally asymmetric hemi-meridian characteristic of a left eye. Further, the right lens can be chiral with respect to the left lens and the four specified hemi-meridian contours of each of the right and left lens can be based on a haptic reference angle calculated for one of the four rotationally asymmetric hemi-meridians of the left or right eye.

In some embodiments, a set of trial scleral lenses can include a right lens configured with specific hemi-meridian contours that each corresponds to a rotationally asymmetric hemi-meridian characteristic of a right eye and a left lens configured with specific hemi-meridian contours that each corresponds to a rotationally asymmetric hemi-meridian characteristic of a left eye. Further, the specified hemi-meridian contours of each of the right and left lens can be based on a haptic reference angle calculated for one of the rotationally asymmetric hemi-meridians of the left or right eye. For example, the trial scleral lenses can be configured with eight or sixteen specific hemi-meridian contours.

In some embodiments, a set of scleral lenses can include a right lens configured with specific hemi-meridian contours that each corresponds to a rotationally asymmetric hemi-meridian characteristic of a right eye and a left lens configured with specific hemi-meridian contours that each corresponds to a rotationally asymmetric hemi-meridian characteristic of a left eye. Further, the specific hemi-meridian contours of each of the right and left lens can be based on a haptic reference angle calculated for one of the rotationally asymmetric hemi-meridians of the left or right eye. In some embodiments, the right lens can be chiral with respect to the left lens.

In some embodiments, a single scleral lens to be applied on an eye can include specific hemi-meridian contours that each corresponds to a rotationally asymmetric hemi-meridian characteristic of an eye; wherein the specific hemi-meridian contours of the lens is based on a haptic reference angle calculated for one of the rotationally asymmetric hemi-meridians of the eye. In some embodiments the scleral lens can be a trial scleral lens and can be configured to be applied on both the right and left eyes.

In some embodiments, the four hemi-meridian contours of each of a left and right eye can be specified as: nasal, temporal, superior and inferior. In some embodiments, the nasal hemi-meridian is the flattest of the four hemi-meridians. In some embodiments, the inferior hemi-meridian is the flattest of the four hemi-meridians. In some embodiments, the temporal hemi-meridian is the flattest of the four hemi-meridians. In some embodiments, the superior hemi-meridian is the flattest of the four hemi-meridians.

In some embodiments, the trial scleral lenses can include two or more pairs of the right and left trial scleral lenses, wherein each pair can be based on a different scleral diameter and/or a different haptic reference angle value.

In some embodiments, a set of trial scleral lenses can include a collection of three pairs of the right and left lenses, wherein each pair can be based on a different scleral diameter. The set of trail scleral lenses can also include three collections of the three pairs of the right and left lenses having different scleral diameters, wherein each collection can be based on a different haptic reference angle value.

In some embodiments, a first of the different haptic reference angle values can represent an average haptic angle calculated for left and right eyes, a second of the different haptic reference angle values can represent one standard deviation less than the average haptic angle calculated for left and right eyes and a third of the different haptic reference angle values can represent one standard deviation greater than the average haptic angle measured for left and right eyes.

In some embodiments, the four specified hemi-meridian contours of the set of trial scleral lenses for each of the right and left sclera can be based on a haptic reference angle calculated for the nasal meridian of the left or right eye. In some embodiments, the haptic reference angle can be calculated for the inferior meridian of the left or right eye. In some embodiments, the haptic reference angle can be calculated for the temporal meridian of the left or right eye. In some embodiments, the haptic reference angle can be calculated for the superior meridian of the left or right eye.

In some embodiments, the left and right lenses of the set of trial scleral lenses can be configured according to spherical scleral contours.

In some embodiments, the configuration of the right and left lenses of the set of trial scleral lenses can include optic portions that can include: a range of front surface optical powers, a range of front surface base and aspheric curves and/or a range of back surface base curves.

In some embodiments, the set of trial scleral lenses can include a right lens configured with four specified hemi-meridian contours that each corresponds to a rotationally asymmetric hemi-meridian characteristic of a right eye having an eye condition and left lens configured with four specified hemi-meridian contours that each corresponds to a rotationally asymmetric hemi-meridian characteristic of a left eye having an eye condition. The eye condition can be irregular/distorted cornea or ocular surface disease.

These and other configurations of the disclosed subject matter will be more fully understood after a review of the following figures and detailed description.

BRIEF DESCRIPTION OF THE DRAWINGS

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of the invention, the scope of which is set forth in the claims that follow.

FIG. 6 shows example sagittal height values for different asymmetric configurations, in accordance with some embodiments of the present disclosure.

DESCRIPTION

The present disclosure relates to trial scleral lenses and the resulting scleral lenses designed for the non-radially symmetric (i.e., rotationally asymmetric) and/or chiral properties of the scleral portion of the eye. In some embodiments, the design of the trial scleral lenses and the resulting scleral lenses also can take into account the specific asymmetric and chiral properties characteristic of eyes with certain conditions or diseases. In some embodiments, the design of the trial scleral lenses and the resulting scleral lenses can also take into account the specific asymmetric properties of the sclera, but not require the lenses to be a pair or chiral in nature. In further embodiments, the trial scleral lenses and the resulting scleral lenses are also designed for the specific asymmetric and chiral properties characteristic of different scleral diameters.

Typically, the lenses used in scleral lens diagnostic fittings are radially symmetric in shape and are referred to as "spherical" in design. Such lenses do not align well with the sclera, which is typically radially asymmetric. Further, each lens is used interchangeably for either the right or left eye. Scleral shape is not only radially asymmetric, it is chiral. The typical shapes of the right and left eyes are mirror images and non-superimposable. Because the trial scleral lenses of the present disclosure take into account the asymmetric and/or chiral properties of the scleral contour, the scleral lenses achieve fit in more eyes with fewer adjustments. Thus, a clinician, using the chiral trial scleral lenses, can more efficiently fit a patient with a satisfactory scleral lens. Further, the resulting lenses designed according to the asymmetric and/or chiral properties of the right or left eye achieve better fit compared to typical scleral lenses that are spherical in shape.

The conditions and diseases that are treated with scleral lenses-fall into two general categories: irregular/distorted cornea and ocular surface disease (OSD). Irregular or distorted cornea is a feature of keratoconus, keratoglobus, pellucid marginal degeneration, Terrien's marginal degeneration, and some eyes that have previously undergone surgery or sustained trauma. OSD encompasses numerous conditions in which there is a malfunction of any or several components of the ocular surface system including the surface and glandular epithelia of the cornea, conjunctiva lacrimal glands, the eyelids and the tear film. Examples of ocular surface disease include Sjögren's syndrome and exposure keratitis. In some embodiments, the trial scleral lenses have a design specific to the irregular/distorted cornea or to ocular surface disease.

The Principles Behind the Design of Asymmetric Chiral Scleral Lenses

Figure 1:
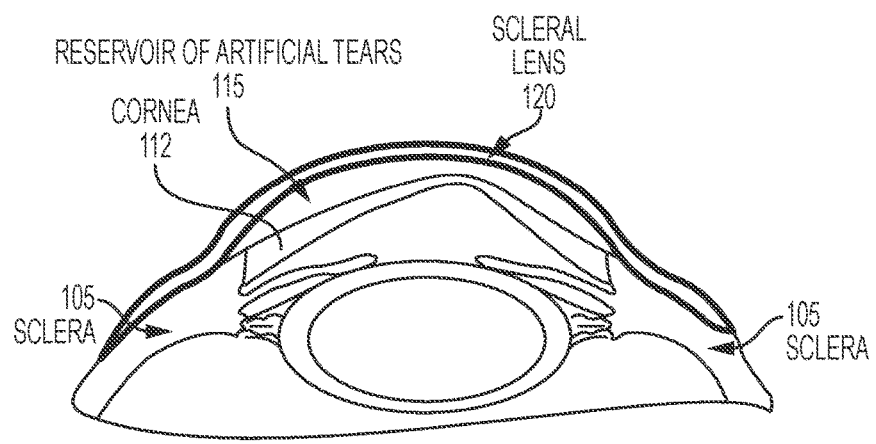
FIG. 1 illustrates a scleral lens vaulting over an irregular cornea and resting on the anterior portion of the sclera.
Figure 2:
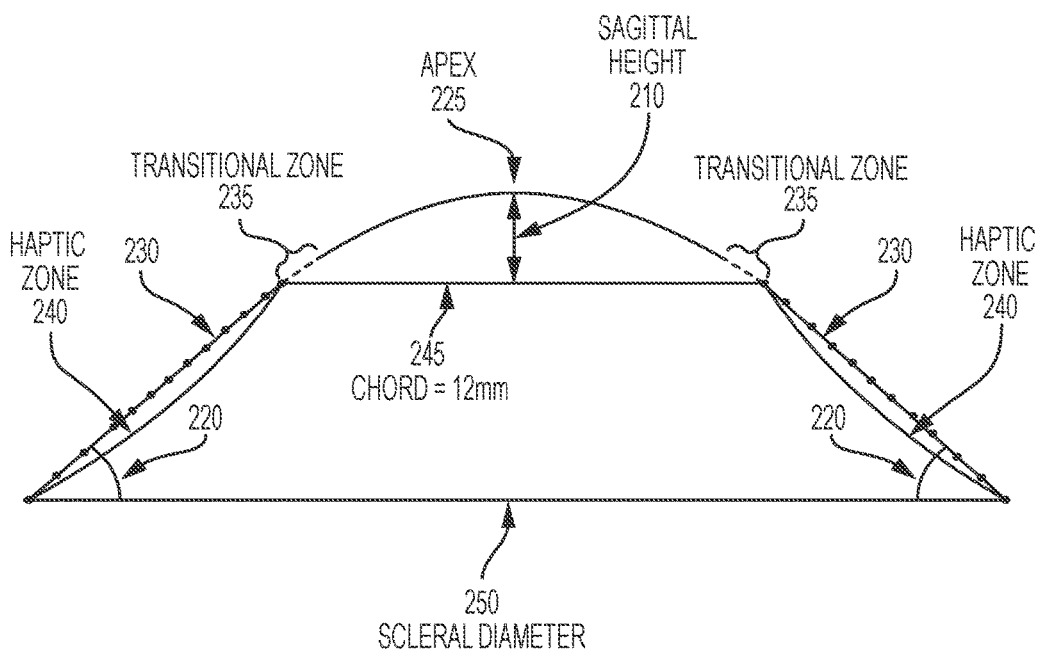
FIG. 2 illustrates example certain parameters that characterize the design of a scleral lens, in accordance with some embodiments of the present disclosure.
Figure 3:
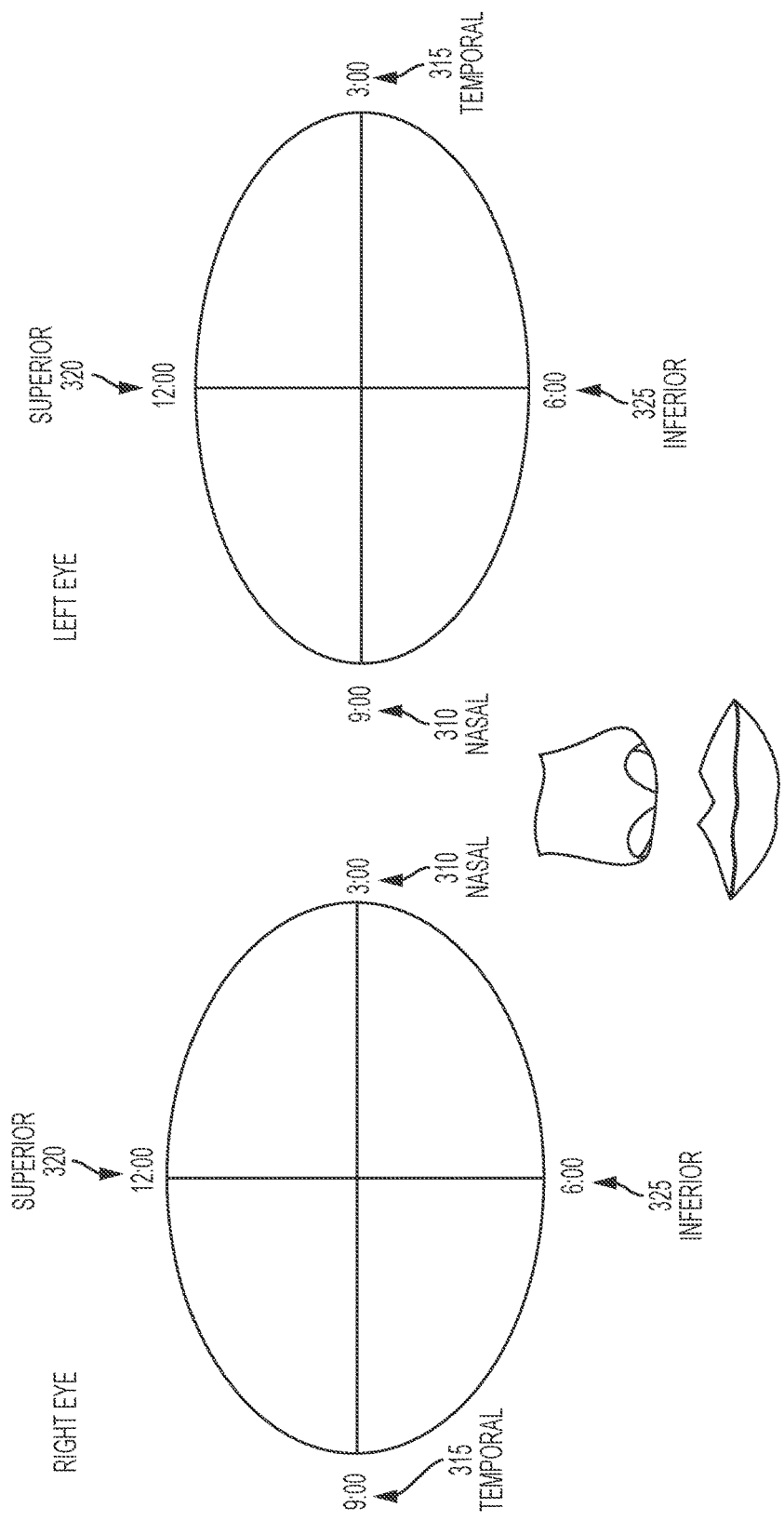
FIG. 3 illustrates an example of the asymmetric shape of the sclera, in accordance with some embodiments of the present disclosure.

The lenses in accordance with some embodiments of the present disclosure are designed according to the asymmetric and chiral shape of the sclera as described in connection with FIG. 3. As shown in FIG. 3, the right and left eyes can be divided into four hemi-meridians: nasal 310, temporal 315, superior 320 and inferior 325, and their location can be described using a clock dial numbering system. The nasal hemi-meridian 310 of the eye corresponds to the reference point that is closest to the nose, (i.e., 3:00 for a right eye and 9:00 for a left eye). The temporal hemi-meridian 315 of the eye corresponds to the reference point that is farthest from the nose (i.e., 9:00 for a right eye and 3:00 for a left eye). The superior and inferior hemi-meridians 320 and 325 of the eye correspond to the points halfway between the nasal and temporal hemi-meridians 310 and 315 toward the forehead and chin respectively (i.e., 12:00 and 6:00 respectively). The haptic deviation refers to the difference in sagittal height of a scleral lens at each of the hemi-meridians. Typically the nasal hemi-meridian 310 of each eye is the flattest. Generally, the superior and inferior hemi-meridians 320 and 325 are steeper than the nasal and temporal hemi-meridians 310 and 315, and the inferior hemi-meridian 325 is the steepest. In keeping with this pattern of characteristically flat and steep hemi-meridians, it becomes clear that the distribution of steepness of the right and left eyes is chiral (i.e., the scleral shape of the left and right eyes are asymmetric in such a way that they are not superimposable). The lenses in accordance with some embodiments of the present disclosure have haptic deviations that are chiral in pattern to match the chirality of scleral steepness. In addition, certain haptic deviations may be characteristic of lenses suitable for treating irregular/distorted cornea as opposed to OSD. One of skill in the art will understand that the nasal hemi-meridian does not have to be the flattest hemi-meridian and any of the four hemi-meridians can be the flattest hemi-meridian. One of skill in the art will also understand that the four hemi-meridians can be further subdivided (e.g., into eight or 16 hemi-meridians). One of skill in the art will also understand that the scleral lenses can be designed according to the asymmetric and/or chiral shape of the sclera.

In some embodiments, as described herein, the trial scleral lenses, as well as the resulting scleral lenses, can have a right eye specific design, or haptic deviations characteristic of a right eye, and a left eye specific design, or haptic deviations characteristic of a left eye, to model the chiral nature of the shape of the right and left eyes respectively.

Figure 4:
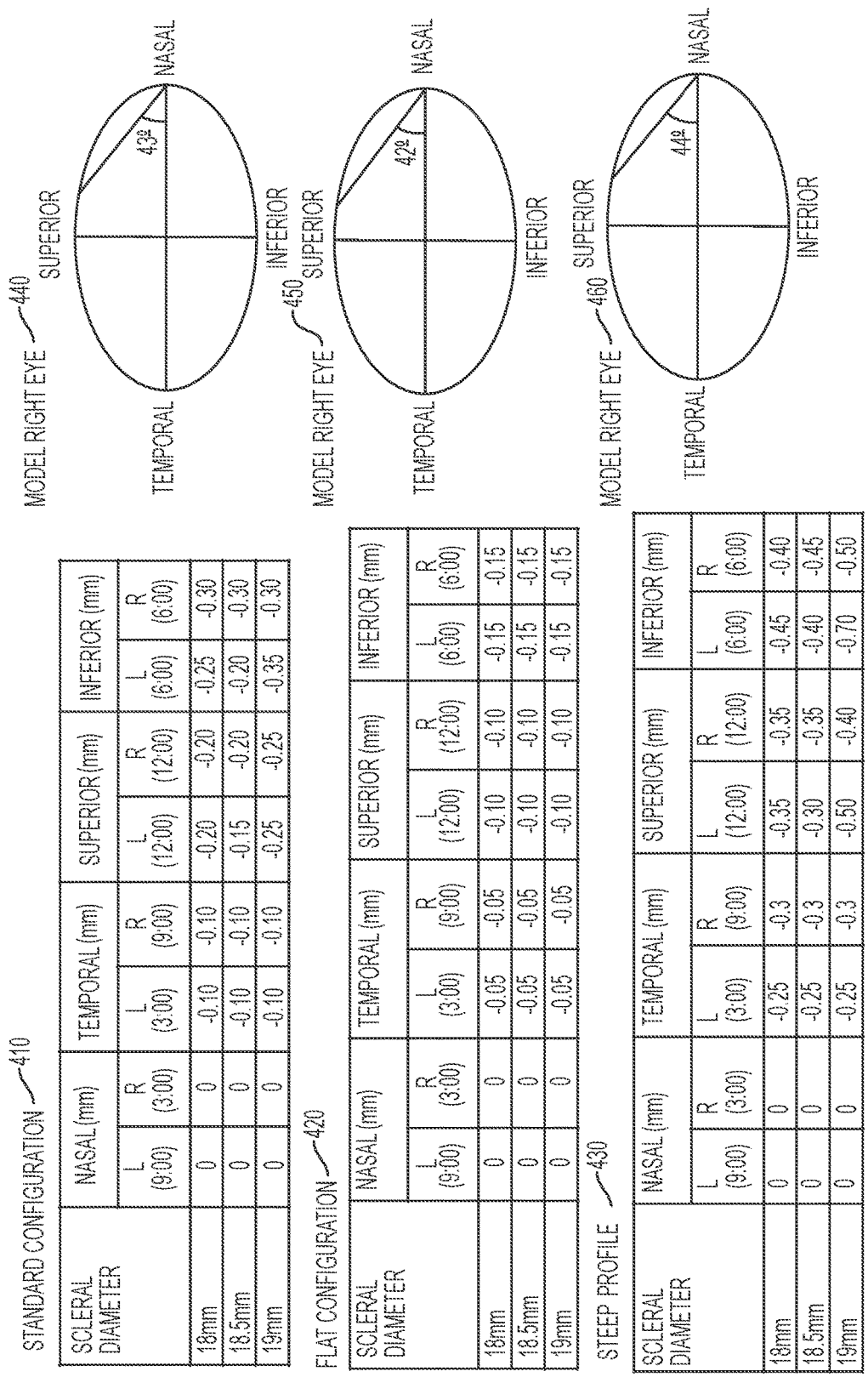
FIG. 4 shows different asymmetric configurations, in accordance with some embodiments of the present disclosure.

For example, FIG. 4 illustrates different configurations of haptic deviations characteristic of right and left eyes. Haptic deviations can be measured in millimeters (or microns) with respect to the flattest or reference hemi-meridian (i.e., the greater the millimeter value the steeper the hemi-meridian). Further, the values shown in the tables for the different haptic deviations are based on the nasal hemi-meridian as the reference and flattest hemi-meridian. For example, for the Standard Configuration 410 associated with the 18 mm scleral diameter, the nasal hemi-meridian has the flattest scleral shape (indicated by "0"), followed by: the temporal hemi-meridian (e.g., 0.10 mm steeper than the nasal hemi-meridian), the superior hemi-meridian (e.g., 0.20 mm steeper than the nasal hemi-meridian) and the inferior hemi-meridian (e.g., 0.25 mm or 0.30 mm steeper than the nasal hemi-meridian). One of skill in the art will understand that the actual values of the haptic deviations may differ from those shown in the tables in FIG. 4. One of skill in the art will also understand that the set of haptic configurations shown in the tables in FIG. 4 can be based on a haptic angle that is calculated for any one of the four or more hemi-meridians of each eye.

In accordance with some embodiments of the present disclosure, the set of haptic configurations referred to herein as the "standard configuration," and shown in the table for Standard Configuration 410, will be based on a haptic reference angle that represents the average haptic angle (e.g., 43°) calculated for right and left eyes. This haptic angle is calculated for the nasal hemi-meridian of each eye (e.g., as shown in Model Right Eye 440), and the scleral asymmetric distributions for the other three hemi-meridians are based on this angle. The table for the Standard Configuration 410 includes a different set of haptic deviations for each of three scleral diameters: 18 mm, 18.5 mm, 19 mm, which reflects the differences in haptic deviation associated with each diameter. One of skill in the art will understand that the scleral diameter may differ from those shown in the tables in FIG. 4.

Another set of haptic deviations referred to herein as the "flat configuration," and shown in the table for Flat Configuration 420, will be based on a haptic angle that represents one standard deviation less (e.g., 42°) than the calculated average haptic angle (e.g., 43°). Like the Standard Configuration 410, this haptic angle is calculated for the nasal hemi-meridian of each eye (e.g., as shown in Model Right Eye 450), and the haptic deviations for the other three hemi-meridians are based on this angle. The table for the Flat Configuration 410 includes a different set of haptic deviations for each of three scleral diameters: 18 mm, 18.5 mm, 19 mm, which reflects the differences in asymmetric distribution associated with each diameter. Overall, the set of haptic deviations associated with the Flat Configuration 420 can be flatter than the set of haptic deviations associated with the Standard Configuration 410.

A third set of haptic deviations, referred to herein as the "steep configuration," and shown in the table for Steep Configuration 430, will be based on a haptic angle that represents one standard deviation greater (e.g., 44°) than the average haptic angle (e.g., 43°). Like the Standard Configuration 410, this haptic angle is calculated for the nasal hemi-meridian of each eye (e.g., as shown for Model Right Eye 460), and the scleral haptic deviations for the other three hemi-meridians are based on this angle. The table for the Steep Configuration 430 includes a different set of haptic deviations for each of three scleral diameters: 18 mm, 18.5 mm, 19 mm, which reflects the differences in asymmetric distribution associated with each diameter. Overall, the set of haptic deviations associated with the Steep Configuration 430 can be steeper than the set of haptic deviations associated with the Standard Configuration 410.

FIG. 4 describes trial scleral lenses, as well as the resulting scleral lenses, designed according to "with-the rule"-scleral contours. "With-the-rule" scleral contours refer to asymmetric distributions of the left and right eyes where the contours of inferior and superior hemi-meridians are steeper than the nasal and temporal hemi-meridians. In other embodiments, trial scleral lenses, as well as the resulting scleral lenses, can be designed according to "against-the-rule" asymmetric distributions, where the inferior and superior hemi-meridians are flatter than the nasal and temporal hemi-meridians. In further embodiments, the trial scleral lenses, as well as the resulting scleral lenses, can be designed according to scleral contour distributions that are spherical and do not exhibit significant differences in haptic deviations at the different hemi-meridians.

A person of skill in the art will understand that the trial scleral lenses, as well as the resulting scleral lens, can be designed as a single scleral lens with specific haptic deviations for a range of scleral diameters that are characteristic of an eye. In some embodiments, a single lens can be designed to be applied on both the right and left eyes and can include specific haptic deviations for a range of scleral diameters that are characteristic of both the right and left eyes.

Figure 5:
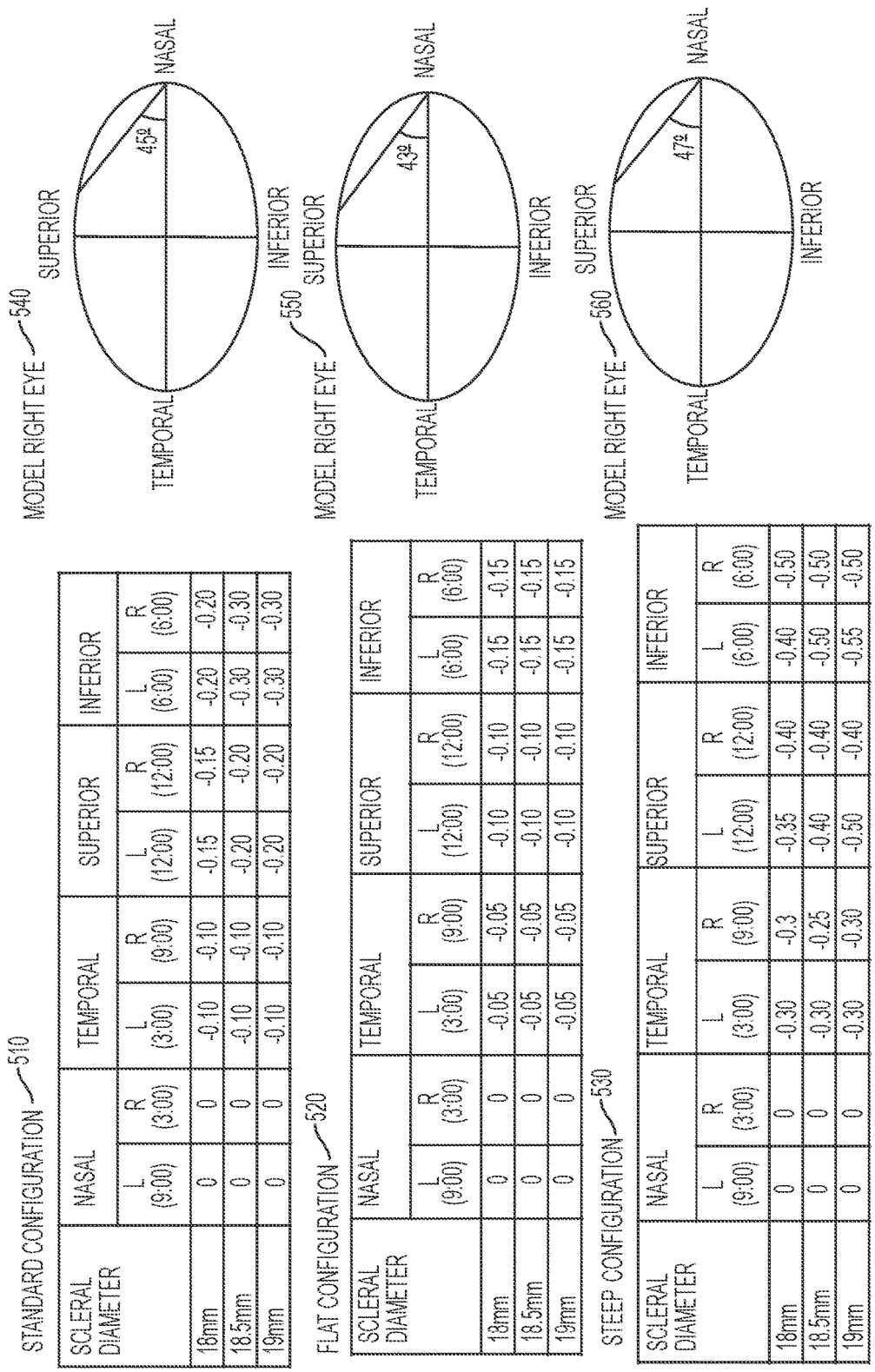
FIG. 5 shows different asymmetric configurations, in accordance with some embodiments of the present disclosure.

In some embodiments, as described herein, the trial scleral lenses, as well as the resulting scleral lenses, can be designed with specific haptic deviations characteristic of eyes with OSD or irregular or distorted cornea. In some embodiments, the configurations of haptic deviations characteristic of right and left eyes with OSD are the same as those described above and shown in FIG. 4. FIG. 5 illustrates different configurations of haptic deviations characteristic of right and left eyes with irregular or distorted cornea. One of skill in the art will understand that the actual values of the haptic deviations may differ from those shown in the tables in FIGS. 4 and 5. One of skill in the art will also understand that the set of haptic configurations shown in the tables in FIGS. 4 and 5 can be based on a haptic angle that is calculated for any one of the four or more hemi-meridians of each eye.

In accordance with some embodiments of the present disclosure, FIG. 5 shows different configurations of haptic deviations characteristic of right and left eyes with irregular or distorted cornea For example, one set of asymmetric configurations, referred to herein as the "standard configuration," and shown in the table for Standard Configuration 510, can be based on a haptic angle that represents the average and reference haptic angle (e.g., 45°) calculated for eyes with irregular or distorted cornea. This haptic angle is calculated for the nasal hemi-meridian of each eye (e.g., as shown for Model Right Eye 540), and the scleral asymmetric distributions for the other three hemi-meridians are based on this angle. The table for the Standard Configuration 510 includes a different set of haptic deviations for each of three scleral diameters: 18 mm, 18.5 mm, 19 mm, which reflects the differences in asymmetric distribution associated with each diameter.

Another set of haptic deviations, referred to herein as the "flat configuration," and shown in the table for Flat Configuration 520, can be based on a haptic angle that represents one standard deviation less (e.g., 43°) than the average haptic angle (e.g., 45°) calculated for eyes with irregular or distorted cornea. Like the Standard Configuration 510, this haptic angle is calculated for the nasal hemi-meridian of each eye (e.g., as shown for Model Right Eye 550), and the scleral asymmetric distributions for the other three hemi-meridians are based on this angle. The table for the Flat Configuration 510, includes a different set of haptic deviations for each of three scleral diameters: 18 mm, 18.5 mm, 19 mm, which reflects the differences in asymmetric distribution associated with each diameter. Overall, the set of haptic deviations associated with the Flat Configuration 520 can be flatter than the set of haptic deviations associated with the Standard Configuration 510.

A third set of haptic deviations, referred to herein as the "steep configuration," and shown in the table for Steep Configuration 530, can be based on a haptic angle that represents one standard deviation greater (e.g., 47°) than the average haptic angle (e.g., 45°) calculated for eyes with an irregular or distorted cornea. Like the Standard Configuration 510, this haptic angle is measured at the nasal hemi-meridian of each eye (e.g., as shown for Model Right Eye 660), and the scleral asymmetric distributions for the other three hemi-meridians are based on this angle. The table for the Steep Configuration 630 includes a different asymmetric configuration for each of three scleral diameters: 18 mm, 18.5 mm, 19 mm, which reflects the differences in asymmetric distribution associated with each diameter. Overall, the set of haptic deviations associated with the Steep Configuration 530 can be steeper than the set of haptic deviations associated with the Standard Configuration 520.

FIG. 5 describes trial scleral lenses, as well as the resulting scleral lenses, designed according to "with-the rule"-scleral contours. "With-the-rule" scleral contours refer to asymmetric distributions of the left and right eyes where the contours of inferior and superior hemi-meridians are steeper than the nasal and temporal hemi-meridians. In other embodiments, the trial scleral lenses, as well as the resulting scleral lenses, can be designed according to "against-the-rule" asymmetric distributions, where the inferior and superior hemi-meridians are flatter than the nasal and temporal hemi-meridians. In further embodiments, trial scleral lenses, as well as the resulting scleral lenses, can be designed according to scleral contour distributions that are spherical and do not exhibit significant differences in haptic deviations at the different hemi-meridians.

In some embodiments, as shown in FIG. 6, the right and left trial scleral lenses, as well as the resulting scleral lenses, including the embodiments designed to treat OSD or irregular or distorted cornea, can also be designed in a range of sagittal heights (e.g., 2.0-5 mm in 0.15 mm increments), but a representative sample for three different sagittal heights are shown for each of the haptic configurations (i.e., standard, flat and step) for each of three diameters (18 mm, 18.5 mm, 19 mm).

Figure 7:
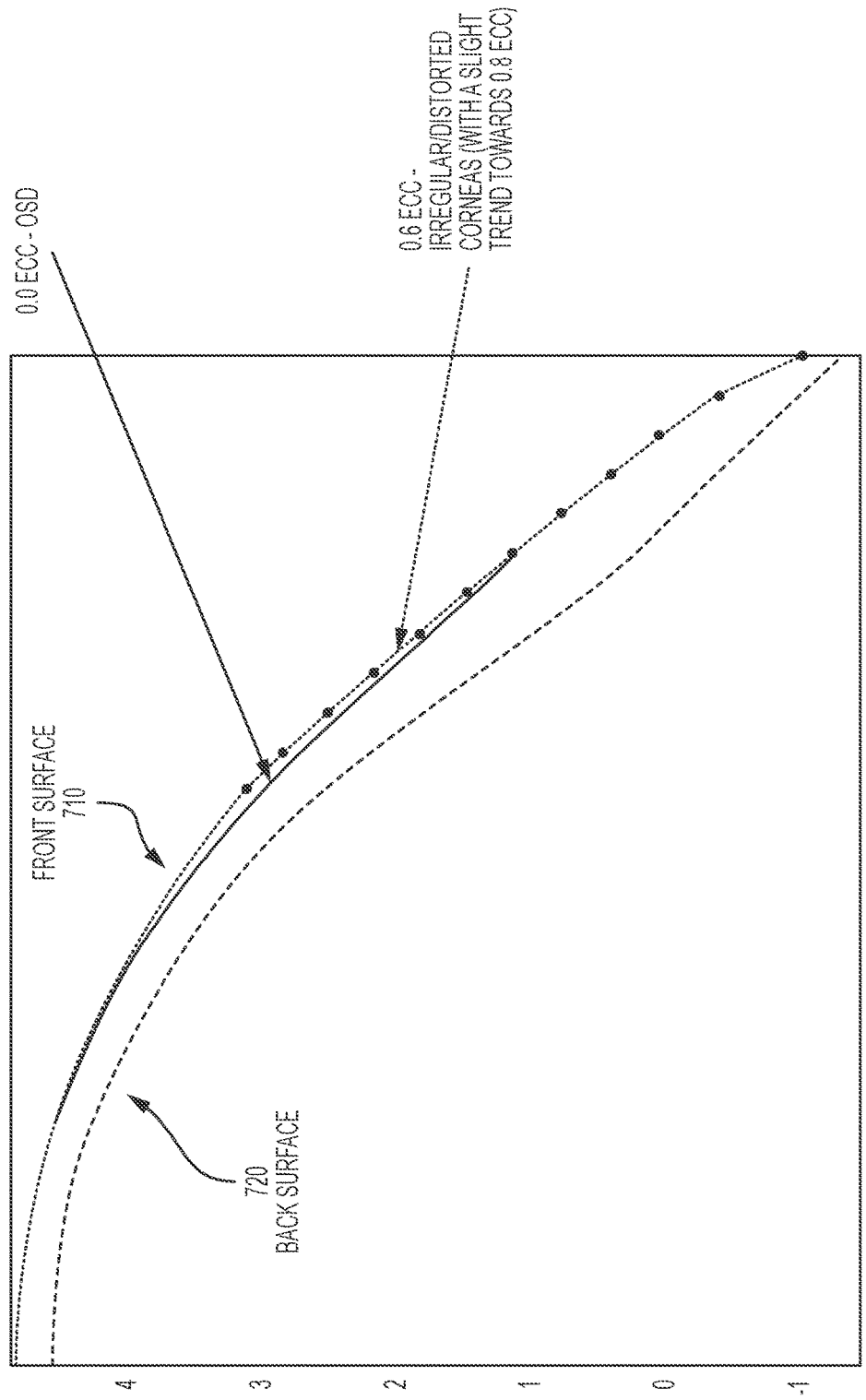
FIG. 7 illustrates the eccentricity values, in accordance with some embodiments of the present disclosure.

In some embodiments, the design of the trial scleral lenses, as well as the resulting scleral lenses, can take into account front surface eccentricity (i.e., the rate of flattening at periphery of the front surface; the higher the eccentricity the more the front surface flattens in the periphery) in order to minimize higher order aberrations and improve best corrected visual acuity (BCVA) (i.e., the best possible vision that an eye can achieve with the use of spectacle lenses, corneal contact lenses, or scleral lenses) for various conditions and diseases. FIG. 7 illustrates the front surface 710 and the back surface 720 of an exemplary quadrant of an eye. The trial scleral lenses, as well as the resulting scleral lenses, can be designed with a varied range of front surface eccentricities (0 to 0.900). To treat OSD, for example, zero front surface eccentricity is sufficient in most cases, whereas 0.6 front surface eccentricity is helpful to treat or correct irregular or distorted cornea. The eccentricity values shown reflect the specific trend in front surface eccentricity to treat OSD and irregular or distorted cornea.

Figure 8:
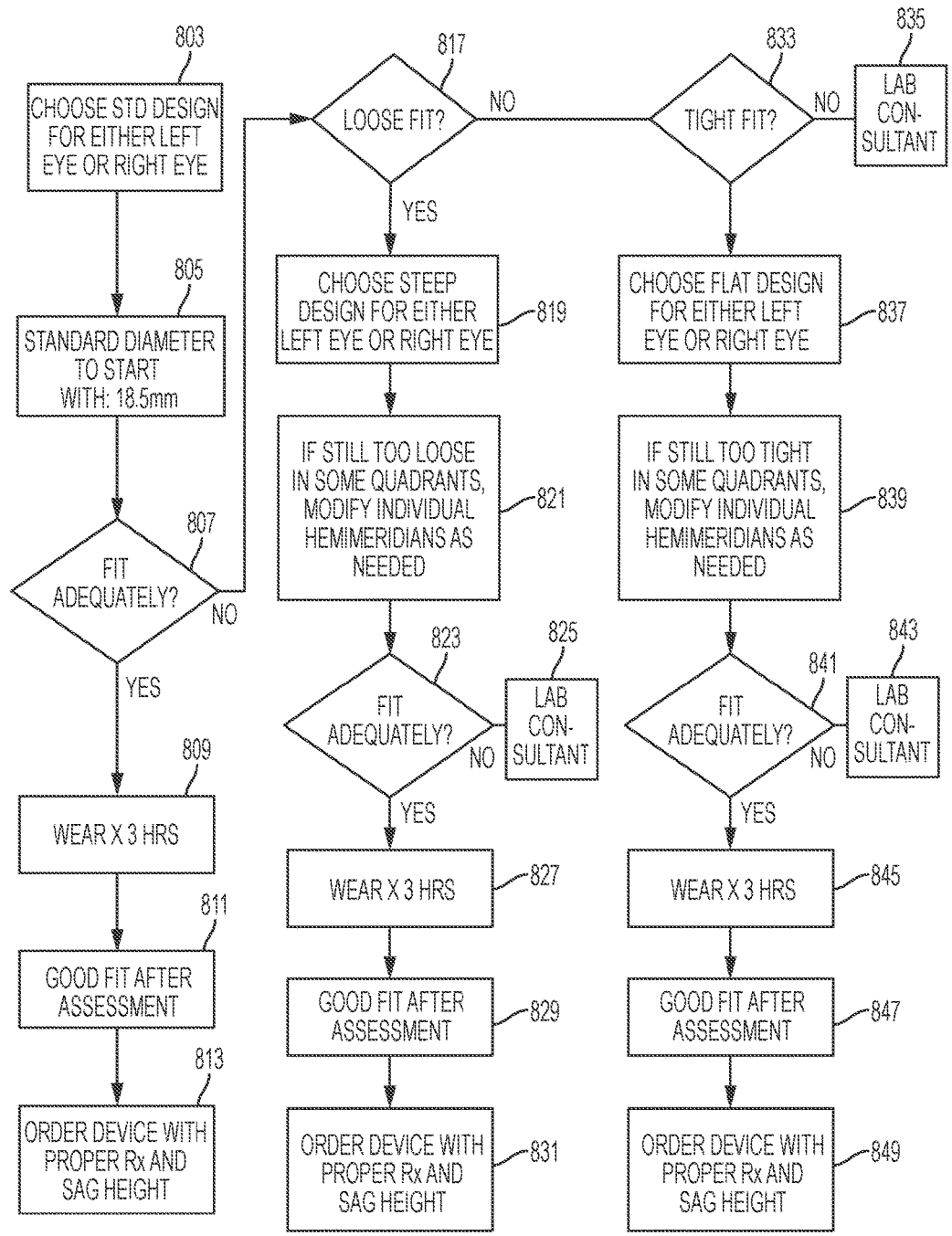
FIG. 8 illustrates the process for selecting and assessing trial lenses, in accordance with some embodiments of the present disclosure.

FIG. 8 shows a flow chart describing the fitting process using the trial scleral lenses, in accordance with an embodiment of the present disclosure. In steps 803 and 805, the right or the left trial lens designed for the standard configuration for an 18.5 mm scleral diameter is selected. In steps 807, 809 and 811, the fit is assessed. If the fit is satisfactory, then the clinician proceeds to order a lens with the necessary front surface optical power and sagittal height (step 1213).

If the fit is too loose (step 817), then the trial lens for either the right or left eye, designed for the steep configuration for scleral diameter 18.5 mm is chosen (step 819). If the trial lens is still too loose in any of the quadrants, then the individual hemi-meridians are modified as necessary (step 821). In steps 823, 827, and 829 the fit is assessed. If the fit is satisfactory, then the clinician proceeds to order a lens with the necessary front surface optical power and sagittal height (step 831).

Similarly, if the fit is too tight, then the trial lens for either the right or left designed for the flat configuration for scleral diameter 18.5 mm is selected (steps 833 and 837). If the trial lens is still too tight in any of the quadrants, then the individual hemi-meridians are modified as necessary (step 839). In steps 841, 845, and 847 the fit is assessed. If the fit is adequate, then the clinician proceeds to order a lens with the necessary front surface optical power and sagittal height (step 849). In some embodiments, a lab consultant may be consulted for particular specifications for the subsequent trial lens (e.g., steps 825, 835, 843).

Figure 9:
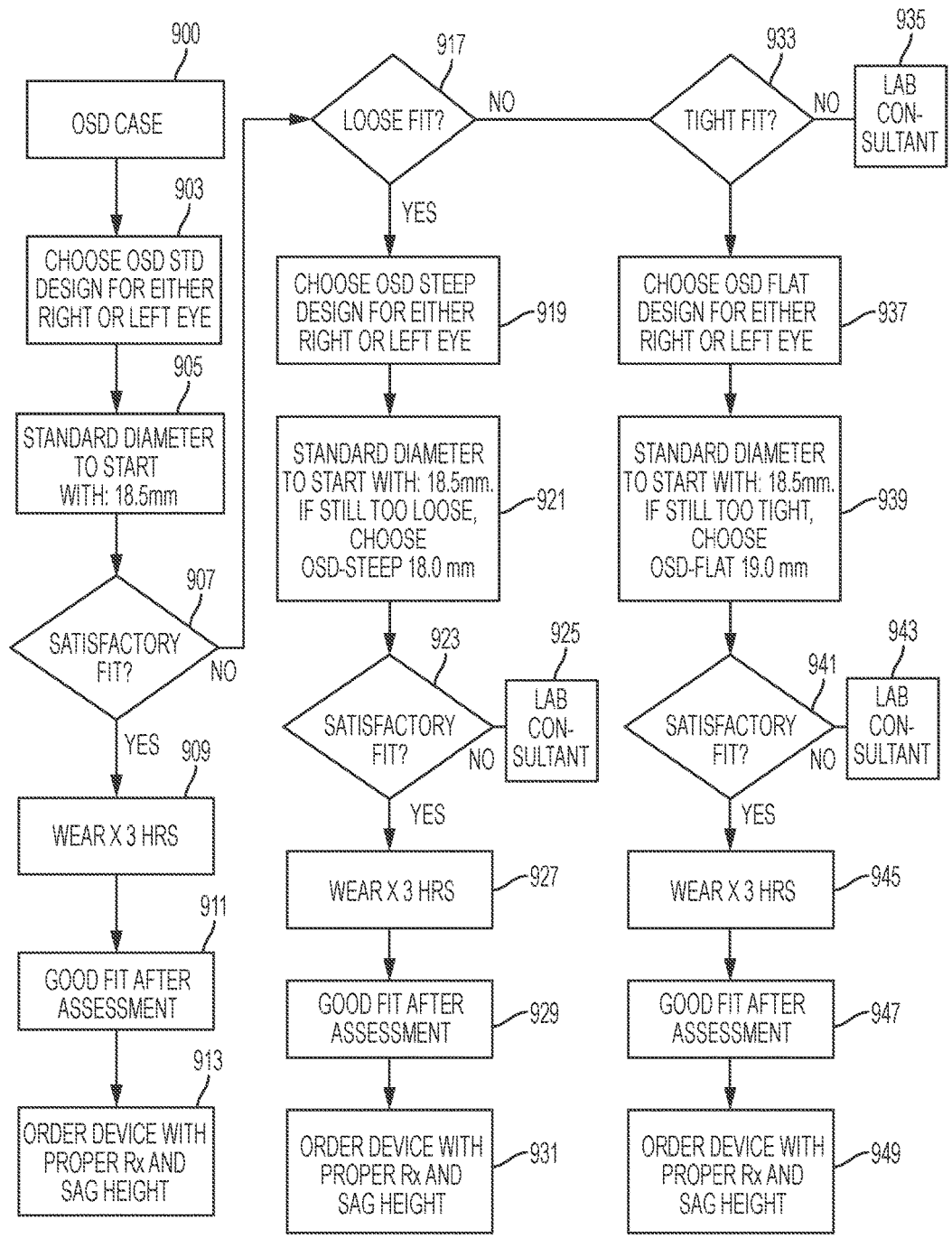
FIG. 9 illustrates the process for selecting and assessing trial lenses, in accordance with some embodiments of the present disclosure.

FIG. 9 shows a flow chart describing the fitting process using the trial scleral lenses, in accordance with an embodiment of the present disclosure. In step 900, the condition or disease of the eye is determined. The right or the left trial lens designed for the standard configuration for OSD for an 18.5 mm scleral diameter is selected (steps 903, 905). In steps 1307, 1309 and 1311, the fit is assessed. If the fit is satisfactory, then the clinician proceeds to order a lens with the necessary front surface optical power and sagittal height (step 913).

If the fit is too loose (step 917), then the trial lens for either the right or left eye, designed for the steep configuration for OSD for scleral diameter 18.5 mm is chosen (step 919). If the trial lens is still too loose, then the 18 mm trial lens for the steep configuration for OSD is selected (step 923). In steps 923, 927 and 929 the fit is assessed. If the fit is satisfactory, then the clinician proceeds to order a lens with the necessary front surface optical power and sagittal height (step 1331).

Similarly, if the fit is too tight, then the trial lens for either the right or left designed for the flat configuration for OSD for scleral diameter 18.5 mm is selected (steps 933, 937, 939). If the trial lens is still too tight, then the 19 mm trial lens is selected (step 939). In steps 941, 945 and 947, the fit is assessed. If the fit is adequate, then the clinician proceeds to order a lens with the necessary front surface optical power and sagittal height (step 949). In some embodiments, a lab consultant may be consulted for particular specifications for the subsequent trial lens (steps 925, 935, 943).

Figure 10A:
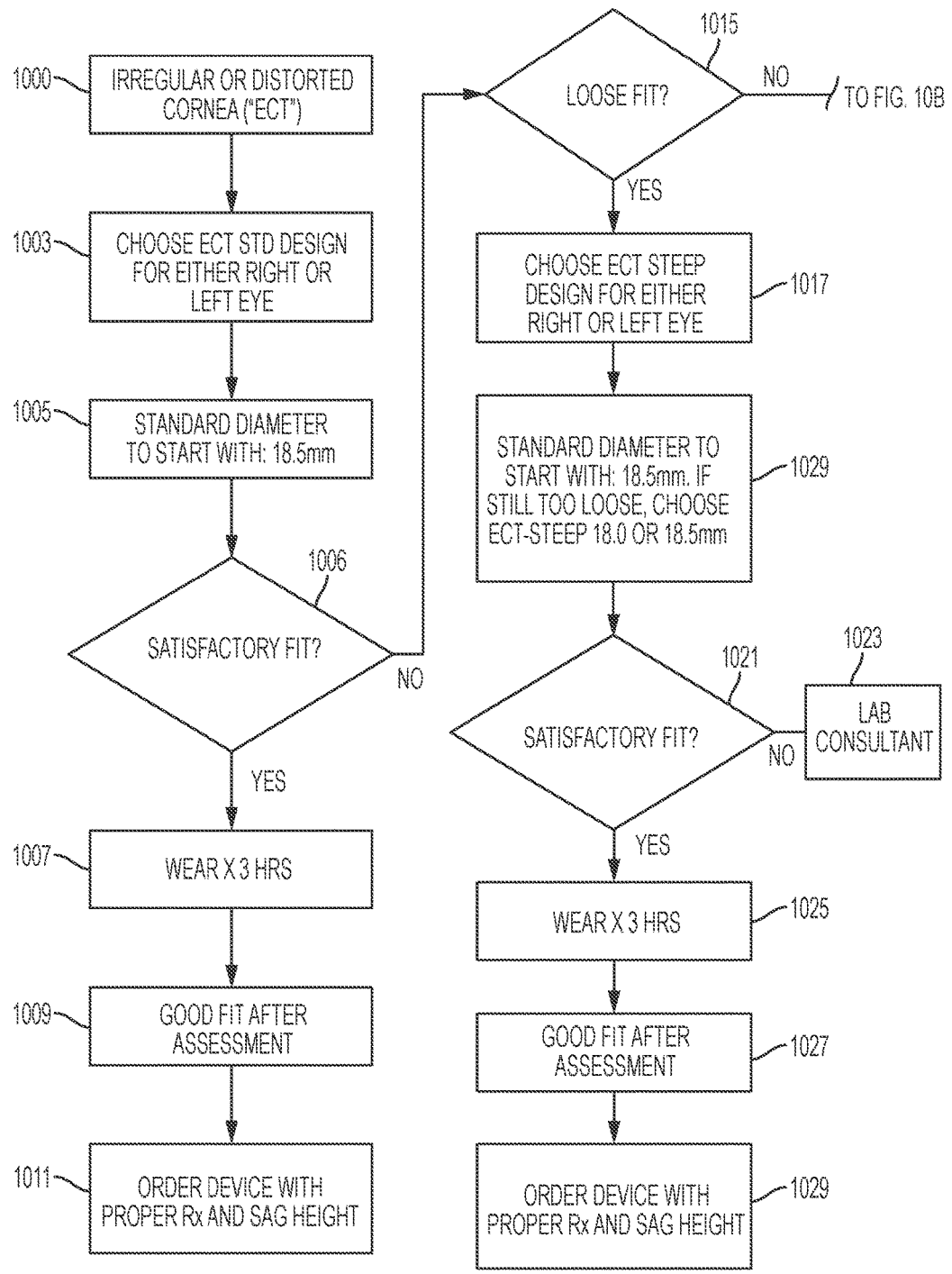
FIGS. 10A-10B illustrate the process for selecting and assessing trial lenses, in accordance with some embodiments of the present disclosure.
Figure 10B:
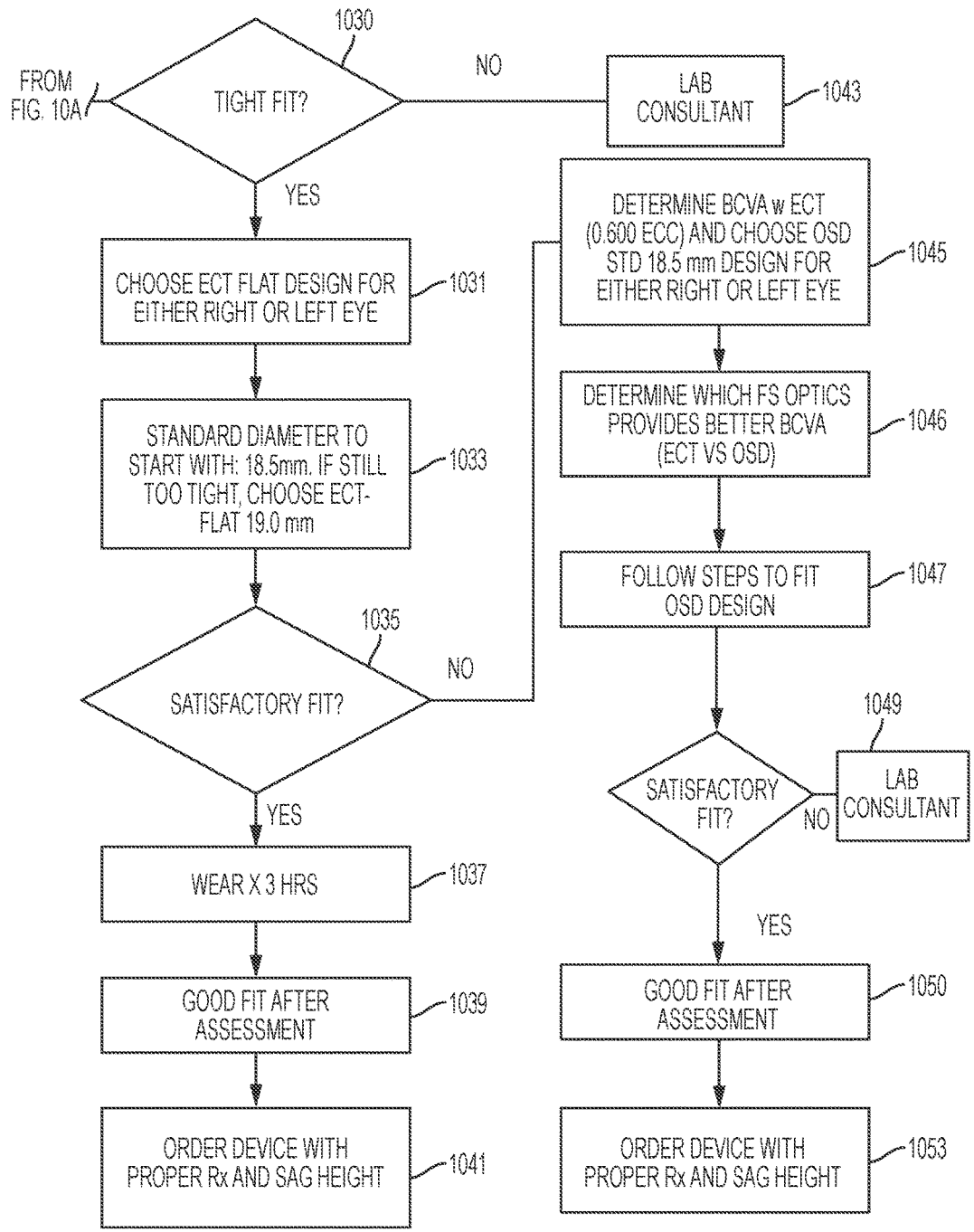

As shown in FIGS. 10A and 10B, similar steps are taken to fit an eye with irregular or distorted cornea with a satisfactory scleral lens. In step 1000, the condition or disease of the eye is determined. If the eye has an irregular or distorted cornea, then a right or left trial designed for the standard configuration for irregular or distorted corneas for an 18.5 mm scleral diameter is selected (steps 1003, 1005).

In steps 1006, 1007, and 1009 the fit is assessed. If the fit is adequate, then the clinician proceeds to order a lens with the necessary optical power and sagittal height (step 1011).

If the fit is too loose (step 1015), then the trial lens for either the right or left eye, designed for the steep configuration for irregular or distorted corneas for an 18.5 mm scleral diameter is selected (steps 1017, 1019). If the trial lens is still too loose, then the 18.0 mm trial lens designed for the steep configuration is selected (step 1019). In steps 1021, 1025, and 1027 the fit is assessed. If the fit is satisfactory, then the clinician proceeds to order a lens with the necessary front surface optical power and sagittal height (step 1029).

Similarly, if the fit is too tight, then the trial lens for either the right or left eye designed for the flat configuration for irregular or distorted corneas for an 18.5 mm scleral diameter is selected (steps 1030, 1031). If the trial lens is still too tight, then the 19.0 mm trial lens designed for the steep configuration is selected (step 1031). In steps 1035, 1037 and 1039 the fit is assessed. If the fit is satisfactory, then the clinician proceeds to order a lens with the necessary front surface optical power and sagittal height (step 1041).

In further embodiments, if the fit is not appropriate (step 1035), then the clinician can compare whether the trial lens designed for OSD, i.e., an 18.5 mm trial lens design for OSD standard configuration provides a better fit. If the OSD design provides a better fit, then at step 1047, the clinician will follow the steps described in FIG. 9 to fit the eye with the trial lenses designed for OSD. Otherwise, in steps 1021, 1025 and 1027, the fit is assessed. If the fit is satisfactory, then the clinician proceeds to order a lens with the necessary front surface optical power and sagittal height (steps 1050, 1053). In some embodiments, a lab consultant can be consulted for particular specifications for the subsequent trial lens (steps 1023, 1043 and 1049).

In some embodiments, the trial scleral lenses and the resulting scleral lenses, including the embodiments designed to treat OSD or irregular or distorted cornea, can be designed with some, or all, of the parameters set forth in the table below and illustrated in FIG. 11:

| Scleral Lenses |
|---|
| Diameter: (16.0-23.0)mm |
| Base Curve: 5.0-9.5 mm |
| Internal Optic Zone: 7.0-12.0 mm |
| Sagittal Depth: 2.0-5.0 mm at 12.0 mm Chord |
| Haptic angle at reference meridian: 42-47° |
| Front surface eccentricity: 0.0-0.9 |
| Hemi-meridian rotationally asymmetric distribution (from flattest to steeper): Nasal, temporal, superior, inferior, and oblique meridians in between |
| 3 haptic configurations: Standard, Flat, Steep |
| Power: Made to order: −20.0 to +20.0D |
| Outer Zone: 10.0-14.0 mm |
| External Optic Zone: 10.0-14.0 mm |
| Center Thickness: 0.20-0.70 mm |
| Junction Thickness 1: 0.30 mm |
| Junction Thickness 2: 0.70 mm |
| Junction Thickness 3: 0.70 mm |
| Edge Thickness: 0.25 mm |

Figure 11:
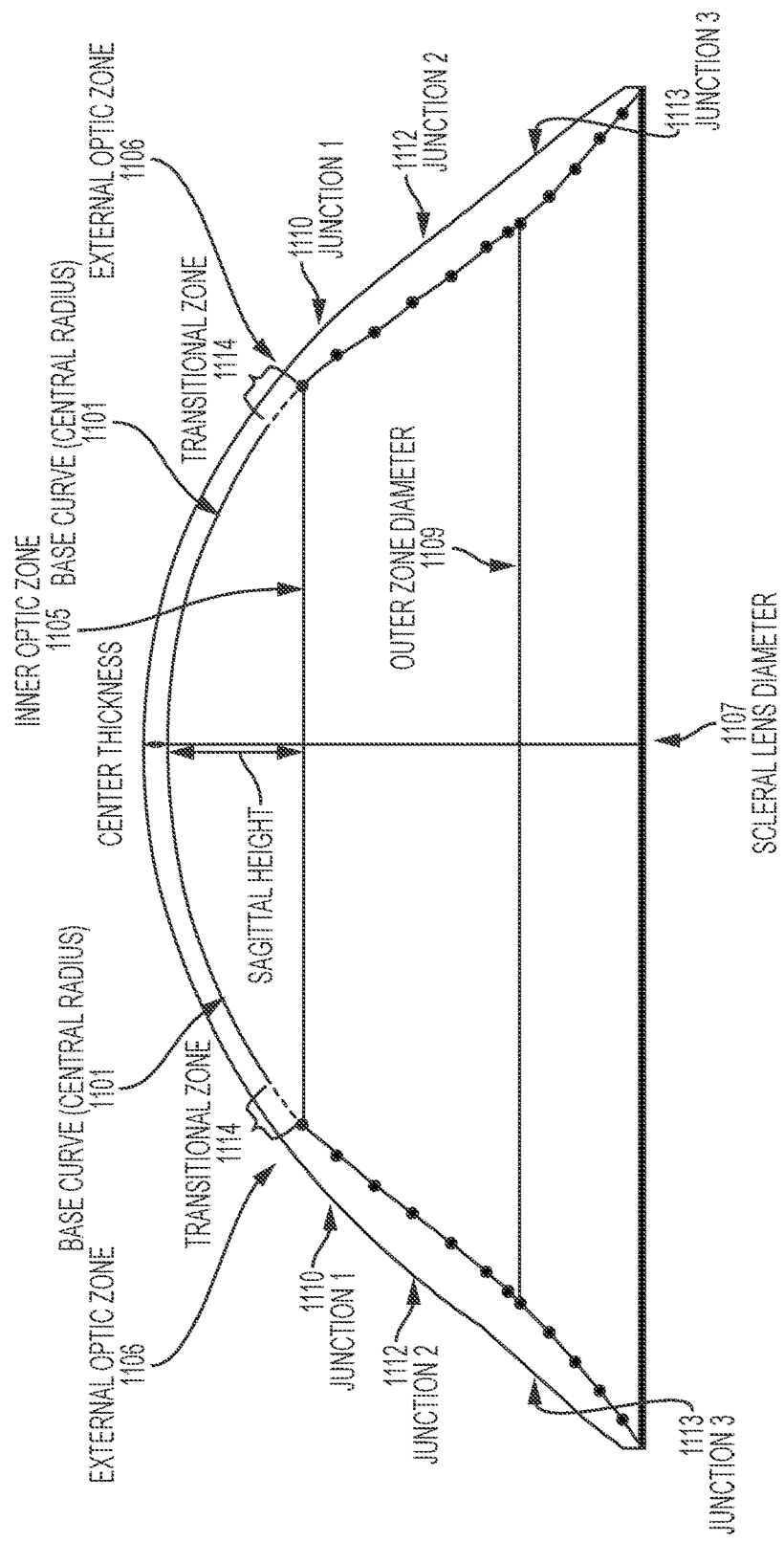
FIG. 11 illustrates certain parameters for modification of a lens, in accordance with some embodiments of the present disclosure.

For example, FIG. 11 shows certain parameters that can be used to design the trial scleral lenses, as well as the resulting scleral lenses, including: three junctions along the peripheral of the lens: junction 1 1110, junction 2 1112 and junction 3 1113. The thickness of each of these junctions can be adjusted. Some representative junction thickness values are listed in the table above. Further, FIG. 11 shows three representative lens diameters: scleral diameter 1107, the outer zone 1109 and the inner optic zone 1105. The inner optic zone 1105 is the central part of the lens that contains optical power for vision correction for a given base curve. As shown in the table above, the front surface optical power is specified for the eye from −20.0 to +20.0 D. Also shown in FIG. 11 is the base curve 1101, which refers to the central radius of the inner optic zone 1105 at the back surface of the lens and the external optic zone 1106, which refers to the outer curve of the inner optic zone at the front surface of the lens 1105.

The trial scleral lenses and the resulting scleral lenses have been described in detail with specific reference to these illustrated embodiments. It will be apparent, however, that various modifications and changes can be made within the spirit and scope of the disclosure as described in the foregoing specification, and such modifications and changes are to be considered equivalents and part of this disclosure.

What is claimed is:

1. A set of trial scleral lenses comprising:
    a right lens configured with four specified hemi-meridian contours that each corresponds to a rotationally asymmetric hemi-meridian characteristic of a right eye;
    a left lens configured with four specified hemi-meridian contours that each corresponds to a rotationally asymmetric hemi-meridian characteristic of a left eye;
    wherein the right lens is chiral with respect to the left lens;
    wherein the four specified hemi-meridian contours of each of the right and left lens are based on a haptic reference angle calculated for one of the four rotationally asymmetric hemi-meridians of the left or right eye; and
    two collections of a plurality of pairs of the right and left lenses, wherein each pair is based on a different scleral diameter, wherein each collection is based on a different haptic reference angle value
    wherein a first of the different haptic reference angle values is about 43°; and
    a second of the different haptic reference angle is about 42°.

2. The set of trial scleral lenses of claim 1 wherein the four specified hemi-meridians contours include: nasal, temporal, superior and inferior.

3. The set of trial scleral lenses of claim 2 wherein the nasal hemi-meridian is the flattest of the four hemi-meridians.

4. The set of trial scleral lenses of claim 2 wherein the inferior hemi-meridian is the flattest of the four hemi-meridians.

5. The set of trial scleral lenses of claim 2 wherein the temporal hemi-meridian is the flattest of the four hemi-meridians.

6. The set of trial scleral lenses of claim 2 wherein the superior hemi-meridian is the flattest of the four hemi-meridians.

7. The set of trial scleral lenses of claim 2 wherein the four specified hemi-meridian contours of each of the right and left lens are based on a haptic reference angle calculated for the nasal meridian of the left or right eye.

8. The set of trial scleral lenses of claim 2 wherein the four specified hemi-meridian contours of each of the right and left lens are based on a haptic reference angle calculated for the inferior meridian of the left or right eye.

9. The set of trial scleral lenses of claim 2 wherein the four specified hemi-meridian contours of each of the right and left lens are based on a haptic reference angle calculated for the temporal meridian of the left or right eye.

10. The set of trial scleral lenses of claim 2 wherein the four specified hemi-meridian contours of each of the right and left lens are based on a haptic reference angle calculated for the superior meridian of the left or right eye.

11. The set of trial scleral lenses of claim 1, wherein the left and right lenses are configured according to spherical scleral contours.

12. The set of trial scleral lenses of claim 1, wherein the configuration of the right and left lenses include optic portions including at least one of a range of front surface optical powers, a range of front surface spherical and aspheric curves, and a range of back surface spherical or aspheric base curves.

13. A set of trial scleral lenses comprising:
    a right lens configured with four specified hemi-meridian contours that each corresponds to a rotationally asymmetric hemi-meridian characteristic of a right eye;
    a left lens configured with four specified hemi-meridian contours that each corresponds to a rotationally asymmetric hemi-meridian characteristic of a left eye;
    wherein the right lens is chiral with respect to the left lens;
    wherein the four specified hemi-meridian contours of each of the right and left lens are based on a haptic reference angle calculated for one of the four rotationally asymmetric hemi-meridians of the left or right eye; and
    two collections of a plurality of pairs of the right and left lenses, wherein each pair is based on a different scleral diameter, wherein each collection is based on a different haptic reference angle value;
    wherein a first of the different haptic reference angle values is about 43°; and
    a second of the different haptic reference angle is about 44°.

14. The set of trial scleral lenses of claim 13 wherein the four specified hemi-meridians contours include: nasal, temporal, superior and inferior.

15. The set of trial scleral lenses of claim 14 wherein the nasal hemi-meridian is the flattest of the four hemi-meridians.

16. The set of trial scleral lenses of claim 14 wherein the inferior hemi-meridian is the flattest of the four hemi-meridians.

17. The set of trial scleral lenses of claim 14 wherein the temporal hemi-meridian is the flattest of the four hemi-meridians.

18. The set of trial scleral lenses of claim 14 wherein the superior hemi-meridian is the flattest of the four hemi-meridians.

19. The set of trial scleral lenses of claim 14 wherein the four specified hemi-meridian contours of each of the right and left lens are based on a haptic reference angle calculated for the nasal meridian of the left or right eye.

20. The set of trial scleral lenses of claim 14 wherein the four specified hemi-meridian contours of each of the right and left lens are based on a haptic reference angle calculated for the inferior meridian of the left or right eye.

21. The set of trial scleral lenses of claim 14 wherein the four specified hemi-meridian contours of each of the right and left lens are based on a haptic reference angle calculated for the temporal meridian of the left or right eye.

22. The set of trial scleral lenses of claim 14 wherein the four specified hemi-meridian contours of each of the right and left lens are based on a haptic reference angle calculated for the superior meridian of the left or right eye.

23. The set of trial scleral lenses of claim 13, wherein each pair of the right and left lenses is based on a different specified sagittal height value.

24. The set of trial scleral lenses of claim 13, wherein the configuration of the right and left lenses include optic portions including at least one of a range of front surface optical powers, a range of front surface spherical and aspheric curves, and a range of back surface spherical or aspheric base curves.

25. A set of trial scleral lenses comprising:
a right lens configured with four specified hemi-meridian contours that each corresponds to a rotationally asymmetric hemi-meridian characteristic of a right eye;
a left lens configured with four specified hemi-meridian contours that each corresponds to a rotationally asymmetric hemi-meridian characteristic of a left eye;
wherein the right lens is chiral with respect to the left lens;
wherein the four specified hemi-meridian contours of each of the right and left lens are based on a haptic reference angle calculated for one of the four rotationally asymmetric hemi-meridians of the left or right eye; and
three collections of a plurality of pairs of the right and left lenses, wherein each pair is based on a different scleral diameter, wherein each collection is based on a different haptic reference angle value;
wherein a first of the different haptic reference angle values is about 45°;
a second of the different haptic reference angle is about 43°.

26. The set of trial scleral lenses of claim 25 wherein the four specified hemi-meridians contours include: nasal, temporal, superior and inferior.

27. The set of trial scleral lenses of claim 26 wherein the nasal hemi-meridian is the flattest of the four hemi-meridians.

28. The set of trial scleral lenses of claim 26 wherein the inferior hemi-meridian is the flattest of the four hemi-meridians.

29. The set of trial scleral lenses of claim 26 wherein the temporal hemi-meridian is the flattest of the four hemi-meridians.

30. The set of trial scleral lenses of claim 26 wherein the superior hemi-meridian is the flattest of the four hemi-meridians.

31. The set of trial scleral lenses of claim 26 wherein the four specified hemi-meridian contours of each of the right and left lens are based on a haptic reference angle calculated for the nasal meridian of the left or right eye.

32. The set of trial scleral lenses of claim 26 wherein the four specified hemi-meridian contours of each of the right and left lens are based on a haptic reference angle calculated for the inferior meridian of the left or right eye.

33. The set of trial scleral lenses of claim 26 wherein the four specified hemi-meridian contours of each of the right and left lens are based on a haptic reference angle calculated for the temporal meridian of the left or right eye.

34. The set of trial scleral lenses of claim 26 wherein the four specified hemi-meridian contours of each of the right and left lens are based on a haptic reference angle calculated for the superior meridian of the left or right eye.

35. The set of trial scleral lenses of claim 25, wherein the left and right lenses are configured according to spherical scleral contours.

36. The set of trial scleral lenses of claim 25, wherein each pair of the right and left lenses is based on a different specified sagittal height value.

37. The set of trial scleral lenses of claim 25, wherein the configuration of the right and left lenses include optic portions including at least one of a range of front surface optical powers, a range of front surface spherical and aspheric curves, and a range of back surface spherical or aspheric base curves.

38. The set of trial scleral lenses of claim 25 comprising:
the right lens configured with four specified hemi-meridian contours that each corresponds to a rotationally asymmetric hemi-meridian characteristic of a right eye having an eye condition;
the left lens configured with four specified hemi-meridian contours that each corresponds to a rotationally asymmetric hemi-meridian characteristic of a left eye having an eye condition;
wherein the eye condition is at least one of irregular/distorted cornea or ocular surface disease.

39. A set of trial scleral lenses comprising:
a right lens configured with four specified hemi-meridian contours that each corresponds to a rotationally asymmetric hemi-meridian characteristic of a right eye;
a left lens configured with four specified hemi-meridian contours that each corresponds to a rotationally asymmetric hemi-meridian characteristic of a left eye;
wherein the right lens is chiral with respect to the left lens;
wherein the four specified hemi-meridian contours of each of the right and left lens are based on a haptic reference angle calculated for one of the four rotationally asymmetric hemi-meridians of the left or right eye; and
three collections of a plurality of pairs of the right and left lenses, wherein each pair is based on a different scleral diameter, wherein each collection is based on a different haptic reference angle value;
wherein a first of the different haptic reference angle values is about 45°;
a second of the different haptic reference angle is about 47°.

40. The set of trial scleral lenses of claim 39 wherein the four specified hemi-meridians contours include: nasal, temporal, superior and inferior.

41. The set of trial scleral lenses of claim 40 wherein the nasal hemi-meridian is the flattest of the four hemi-meridians.

42. The set of trial scleral lenses of claim 40 wherein the inferior hemi-meridian is the flattest of the four hemi-meridians.

43. The set of trial scleral lenses of claim 40 wherein the temporal hemi-meridian is the flattest of the four hemi-meridians.

44. The set of trial scleral lenses of claim 40 wherein the superior hemi-meridian is the flattest of the four hemi-meridians.

45. The set of trial scleral lenses of claim 40 wherein the four specified hemi-meridian contours of each of the right and left lens are based on a haptic reference angle calculated for the nasal meridian of the left or right eye.

46. The set of trial scleral lenses of claim 40 wherein the four specified hemi-meridian contours of each of the right and left lens are based on a haptic reference angle calculated for the inferior meridian of the left or right eye.

47. The set of trial scleral lenses of claim 40 wherein the four specified hemi-meridian contours of each of the right and left lens are based on a haptic reference angle calculated for the temporal meridian of the left or right eye.

48. The set of trial scleral lenses of claim 40 wherein the four specified hemi-meridian contours of each of the right and left lens are based on a haptic reference angle calculated for the superior meridian of the left or right eye.

49. The set of trial scleral lenses of claim 39, wherein the left and right lenses are configured according to spherical scleral contours.

50. The set of trial scleral lenses of claim 39, wherein each pair of the right and left lenses is based on a different specified sagittal height value.

51. The set of trial scleral lenses of claim 39, wherein the configuration of the right and left lenses include optic portions including at least one of a range of front surface optical powers, a range of front surface spherical and aspheric curves, and a range of back surface spherical or aspheric base curves.

52. The set of trial scleral lenses of claim 39 comprising:
- the right lens configured with four specified hemi-meridian contours that each corresponds to a rotationally asymmetric hemi-meridian characteristic of a right eye having an eye condition;
- the left lens configured with four specified hemi-meridian contours that each corresponds to a rotationally asymmetric hemi-meridian characteristic of a left eye having an eye condition;

wherein the eye condition is at least one of irregular/distorted cornea or ocular surface disease.

\* \* \* \* \*